US007157083B2

(12) United States Patent
Gallina

(10) Patent No.: US 7,157,083 B2
(45) Date of Patent: Jan. 2, 2007

(54) COMPOSITIONS AND METHODS FOR TREATING RETROVIRAL INFECTIONS

(75) Inventor: Damian J. Gallina, Erie, PA (US)

(73) Assignee: Surrogate Pharmaceutical Pathways, LLC, Erie, PA (US)

( * ) Notice: Subject to any disclaimer, the term of this patent is extended or adjusted under 35 U.S.C. 154(b) by 237 days.

(21) Appl. No.: 10/050,655

(22) Filed: Jan. 16, 2002

(65) Prior Publication Data

US 2002/0164321 A1 Nov. 7, 2002

Related U.S. Application Data

(63) Continuation-in-part of application No. 09/305,801, filed on Apr. 22, 1999, now abandoned.

(60) Provisional application No. 60/082,185, filed on Apr. 23, 1998.

(51) Int. Cl.
*A61K 38/47* (2006.01)
*A61K 39/21* (2006.01)

(52) U.S. Cl. ................................ 424/94.61; 424/208.1

(58) Field of Classification Search ............ 424/96.62, 424/208.1, 94.1, 94.61
See application file for complete search history.

(56) References Cited

U.S. PATENT DOCUMENTS

| | | | |
|---|---|---|---|
| 5,079,236 | A | 1/1992 | Drizen et al. |
| 5,529,987 | A | 6/1996 | Gallina |
| 5,550,112 | A | 8/1996 | Gallina |
| 5,583,118 | A | 12/1996 | Gallina |
| 5,583,119 | A | 12/1996 | Gallina |
| 5,583,120 | A | 12/1996 | Gallina |
| 5,624,915 | A | 4/1997 | Gallina |
| 5,631,242 | A | 5/1997 | Gallina |
| 5,679,655 | A | 10/1997 | Gallina |
| 5,897,880 | A | 4/1999 | Drizen et al. |
| 6,007,843 | A | 12/1999 | Drizen et al. |
| 6,063,405 | A | 5/2000 | Drizen et al. |
| 6,120,804 | A | 9/2000 | Drizen et al. |
| 6,335,034 | B1 | 1/2002 | Drizen et al. |
| 6,335,035 | B1 | 1/2002 | Drizen et al. |
| 6,346,271 | B1 | 2/2002 | Drizen et al. |
| 6,387,407 | B1 | 5/2002 | Drizen et al. |
| 6,797,267 | B1 * | 9/2004 | Horwitz .................. 424/93.71 |

OTHER PUBLICATIONS

Freshney (Culture of Animal Cells, A Manual of Basic Technique, Alan R. Liss, Inc., 1983, New York entire document especiall p. 4).*

Guo, (The Role of CD$$ in HIV), Dissertation Abstracts International, (1996), vol. 57, No. 1B, p. 255).*

Francis Szoka, et al., "*Mechanism of Targeting to CD44 Positive Breast Tumors*", University of California, San Francisco—School of Pharmacy, Abstract p. # A-13.

Pruimboom, et al., "Capsular Hyaluronic Acid-mediated Adhesion of *Pasteurella multocida* to Turkey Air Sac Macrophages", Avian Disease, 1996, vol. 40, pp. 887-893.

H. L. Kain, "Experimentelle Untersuchungen zur proliferativen Vitreoretinopathie (PVR)", Fortschr Ophthalmol, 1991, vol. 88, pp. 671-676.

Stanescu et al., "Interaction Between macrophages And Articular Surfaces: An In Vitro Transmission And Scanning Electron Microscopy Study", Connective Tissue Research, 1990, vol. 24, pp. 207-218.

Shannon et al., "Participation of Hyaluronic Acid In The Macrophage Disappearance Reaction", Immunological Communications, 1980, vol. 9, No. 4, pp. 357-370.

Sun, et al., "Expression Profile of Hyaluronidase mRNA Transcripts in the Kidney and in Renal Cells", Kidney blood Press Research, 1998, vol. 21, pp. 413-418.

Van der Gaag, et al., "The Influence Of High Molecular Weight Sodium Hyaluronate (Healon®) On The Production Of Migration Inhibitory Factor", IRL Press Limited, 1987, vol. 6, pp. 1433-1440.

Culty, et al., "The Hyaluronan Receptor (CD44) Participates in the Uptake and Degradation of Hyaluronan", The Journal of Cell Biology, vol. 116, No. 4, Feb. 1992, pp. 1055-1062.

Poermadjaja, et al., "Phagocytic Uptake and Killing of Virulent And Avirulent Strains of *Pasteurella Multocida* of Capsular Serotype A By Chicken Macrophages", Veterinary Microbiology, 2000, vol. 72, pp. 163-171.

Khaldoyanidi et al., "Hyaluronate-Enhanced Hematopoiesis: Two Different Receptors Trigger the Release of Interleukin-1β and Interleukin-6 From bone Marrow Macrophages", Blood, Aug. 1, 1999, vol. 94, No. 3, pp. 940-949.

De Carvalho et al., "Effect of Various Digestive Enzymes On The Interaction of Toxoplasma Gondii With Macrophages", Parasitol Research, 1993, vol. 79, pp. 114-118.

Denhardt, et al., "Osteopontin As A Means To cope With Environmental Insults: Regulation Of Inflammation, Tissue Remodeling, And Cell Survival", The Journal of Clinical Investigation, May 2001, vol. 107, No. 9, 1055-1061.

Denhardt, et al., "Role of Osteopontin In Cellular Signaling And Toxicant Injury", Annual Review of Pharmacology and Toxicology, 2001, vol. 41, pp. 723-749.

(Continued)

*Primary Examiner*—Christopher Tate
*Assistant Examiner*—Randall Winston
(74) *Attorney, Agent, or Firm*—McDonnell Boehnen Hulbert & Berghoff LLP

(57) ABSTRACT

The present invention relates to hyaluronidase enzyme methods, vaccines and compositions for treating or preventing pathogenic infections, such as HIV, in a patient. The invention also relates to methods, vaccines and compositions for providing immunity against HIV infection in a patient comprising treating the patient with HIV virus or HIV infected cells that have been treated with hyaluronidase.

9 Claims, No Drawings

OTHER PUBLICATIONS

Leite-de-Moraes, et al., "Natural Killer T Cells: A Potent Cytokine-Producing Cell Population", European Cytokine Network, Sep. 1997, vol. 8, Issue 3, pp. 229-237.

Oswald, et al., "Tumor Necrosis Factor Is Required For The Priming of Peritoneal Macrophages By Trehalose Dimycolate", European Cytokine Network, Dec. 1999, vol. 10, Issue 4, pp. 533-540.

* cited by examiner

COMPOSITIONS AND METHODS FOR TREATING RETROVIRAL INFECTIONS

This application is a continuation in part of U.S. application Ser. No. 09/305,801, filed Apr. 22, 1999 now abandoned which claims priority from provisional application 60/082,185, filed Apr. 23, 1998. U.S. application Ser. No. 09/305,801 is herein incorporated by reference in its entirety.

BACKGROUND OF THE INVENTION

1. Field of the Invention

This invention relates to hyaluronidase compositions and methods for the effective treatment and prevention of pathogen infection, including retroviral infections such as HIV. The invention also relates to novel methods for developing and eliciting immune responses to pathogen infections, including retroviral infections such as HIV.

2. Description of the Related Art

Hyaluronidase enzymes are found throughout the animal kingdom and exist as hydrolytic, transglycosidic and mucolytic proteins. There are essentially two types of hyaluronidase: the non-specific type which breaks down hyaluronic acid, chondroitin and related polysaccharides; and the type which specifically cleaves hyaluronic acid. Hyaluronidases of varying molecular weights, composition, and activity are available from numerous sources including bacteria (via fermentation, etc.) various cell lines (including human) and animal testes.

Hyaluronidase has been used for the treatment of tumors (U.S. Pat. No. 6,193,963); for accelerating the clearance of hemorrhagic blood from the vitreous humor of the eye (U.S. Pat. No. 6,039,943); to reduce intraocular pressure in the eyes of glaucoma patients through degradation of hyaluronan within the vitreous humor (U.S. Pat. No. 4,820,516); as a “spreading agent” to enhance the activity of chemotherapeutics and/or the accessibility of tumors to chemotherapeutics (Czejka, et al., *Pharmazie* 1990, 45(9), 693–4); in the prevention and treatment of helmith infections (U.S. Pat. No. 5,811,100); and for treating benign prostatic hypertrophy (U.S. Pat. No. 5,116,615).

The primary substrate for the hyaluronidase enzyme is hyaluronic acid. Hyaluronic acid is a well known substance that is found in joint tissue and in the vitreous humor of the eye of mammals. Hyaluronic acid is also an integral part of many cell wall structures and has been extracted from rooster combs, human umbilical cords and bacterial cultures. It is a naturally occurring mucopolysaccharide with a molecular weight generally ranging between 50,000 and 8,000,000 (or possibly higher or lower), depending on the source of the material, the analytical method used in its determination and isolation technique.

The terms “haluronate” or “hyaluronan” and the abbreviation “HA” are often used to mean “hyaluronic acid equivalent” indicating hyaluronic acids of varying molecular weights, any of its salt forms, derivatives, isoforms, and/or ligand complexes.

The HIV virus utilizes hyaluronic acid in the adhesion process enabling the virus to bond to different cell lineages. For example, it has been reported that HIV can bind to hyaluronic acid through acquired CD44 adhesion molecules and its isoforms and retain its biological activity when expressed on the virus (*J. Immunol.* 1996, 156(4), 1557–1565; AIDS *Res. Hum. Retroviruses* 1995, 11(9), 1007–1113).

Described herein are hyaluronidase compositions and methods of using said compositions for the prevention and/or treatment of retroviral infections, such as HIV infection, in mammals.

BRIEF DESCRIPTION OF THE INVENTION

The present invention relates to hyaluronidase compositions for the treatment and prevention of retroviral infections. The present invention also relates to methods of using hyaluronidase compositions for treatment and/or prevention of retroviral infections.

Accordingly, in one aspect, this invention relates to compositions and prodrug compositions for providing immunity against HIV infection, for preventing HIV infection and/or for treating HIV infection in a mammal, said compositions comprising hyaluronidase.

In another aspect, this invention relates to methods for providing immunity against HIV infection, for preventing HIV infection and/or for treating HIV infection in a mammal in need of HIV immunity, prevention, or treatment, comprising administering an effective amount of a composition comprising hyaluronidase.

In yet another aspect, this invention relates to compositions for providing immunity against HIV infection, for preventing HIV infection and/or for treating HIV infection in a mammal, said composition comprising hyaluronidase treated virus. The virus can be further attenuated or inactivated, for example, by heat treatment.

In still another aspect, this invention relates to methods for providing immunity against HIV infection, for preventing HIV infection and/or for treating HIV infection in a mammal, comprising administering treatments that consist of hyaluronidase treated virus. The virus can be further attenuated or inactivated, for example, by heat treatment.

The invention described herein demonstrates that antigen presenting cells, such as macrophages and monocytes, will internalize hyaluronidase treated virus and initiate an appropriate and competent immune response to HIV and other retroviruses.

The invention described herein also demonstrates that antigen presenting cells can initiate the same degree of immune response when co-cultured with hyaluronidase treated dead virus or with hyaluronidase treated live virus.

The invention described herein also provides a method for the development of therapeutic and prophylactic vaccines as well as therapeutic parenteral formulations.

The invention described herein further provides for the use of hyaluronidase as a means and method to augment immune response to virus, antigen and/or immunogen.

DETAILED DESCRIPTION OF THE PREFERRED EMBODIMENTS

As used in this specification, the term “inactivated virus” refers to viral pathogens that have been killed, for example, by heat treatment or chemical treatment.

As used in this specification, the term “attenuated virus” refers to live viral pathogens capable of replication but which are not pathogenic.

This invention relates to hyaluronidase compositions and methods for treating retroviral infections, such as HIV infections, using hyaluronidase, hyaluronidase treated virus, or hyaluronidase treated virally infected cells. The invention also provides compositions and methods for providing immunity against HIV in mammals. The compositions of the present invention are comprised of hyaluronidase enzyme.

One of the problems associated with treating HIV infection is that the antigen presenting cell 'presentation' is either missing or infectiously impaired in HIV infection. It is believed that the reason for the poor efficacy of either chemically treated HIV or heat inactivated HIV vaccines, therefore, is the inability of Antigen Presenting Cells to recognize, internalize and phagocytize the killed or denatured virus. Thus, the initial Antigen Presenting Cell step is severely limited or absent altogether. In addition to not recognizing dead or living HIV as an immunogen or antigen, the putative Th1 on/off switch necessary for a cellular response, the CD44 receptor, is not innervated. Also, in order to elicit cellular immunity the APC must internalize, analyze and recognize a "self-identifying marker" such as the non-antigenic or anti-antigenic viral envelope.

This invention provides compositions, vaccine compositions and methods of treatment which overcome the above problems associated with the treatment of HIV. Disclosed herein is the discovery that the hyaluronidase enzyme exhibits adverse and toxic effects against HIV infected cells. This adverse activity results in significantly reduced viral replication within the infected cell. Thus the hyaluronidase enzyme is capable of treating HIV infected cells in an HIV infected patient.

Further, the treatment of the HIV virus itself with the hyaluronidase enzyme creates an effective antigen or immunogen capable of eliciting an immune response against the virus. Thus hyaluronidase is capable of directly reducing or eliminating the HIV virus from an infected patient.

Antigen Presenting Cells (APCs), such as monocytes and macrophages, process hyaluronidase treated HIV infected cells or hyaluronidase treated virus in a different manner than non-hyaluronidase treated infected cells. Hyaluronidase treated cells or virus, unlike non-hyaluronidase treated cells or virus, are more readily recognized and internalized by APCs thus permitting the APCs to stimulate an immune response to the virus. Therefore, the treatment of HIV virus or infected cells with hyaluronidase allows naïve immunocytes to recognize the HIV virus and be resistant to HIV challenge. These results permit the development of therapeutic and prophylactic vaccines and therapeutic parenteral formulations.

Without wishing to be bound by any particular theory, it is believed that hyaluronidase is the binding molecule between cellular hyaluronic acid and the APC and signals the APC to become a "host" or "autotropic" APC. Because of this, hyaluronidase can also bridge antigen to APC. As a result, when inactivated virus or virally infected cells are treated with hyaluronidase a proper and competent cell-mediated immune response to HIV infection is elicited.

The compositions of the invention may be formulated as a solution of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxy cellulose, acacia, polyethylene glycol, mannitol, sodium chloride or sodium citrate.

The compositions of the invention can also be used as a vaccine, by compounding the enzyme with a suitable adjuvant or excipient of the kind conventionally employed in vaccine formulations. Vaccine formulations of the present invention comprise an immunogenic amount of a live or inactivated or attenuated virus treated with hyaluronidase as disclosed herein in combination with a pharmaceutically acceptable carrier. An "immunogenic amount" is an amount of the hyaluronidase treated virus sufficient to evoke an immune response. Exemplary pharmaceutically acceptable carriers include, but are not limited to, sterile pyrogen-free water and sterile pyrogen-free physiological saline solution.

Administration of the vaccines disclosed herein may be carried out by any suitable means, including both parenteral injection (such as intraperitoneal, subcutaneous, or intramuscular injection), and by topical application of the vaccine (typically carried in the pharmaceutical formulation) to an airway surface. Topical application of the vaccine to an airway surface can be carried out by intranasal administration (e.g. by use of dropper, swab, or inhaler which deposits a pharmaceutical formulation intranasally). Topical application of the vaccine to an airway surface can also be carried out by inhalation administration, such as by creating respirable particles of a pharmaceutical formulation (including both solid particles and liquid particles) containing the hyaluronidase treated virus as an aerosol suspension, and then causing the subject to inhale the respirable particles. Methods and apparatus for administering respirable particles of pharmaceutical formulations are well known, and any conventional technique can be employed. The vaccines of the present invention can also be administered intravenously, such as by IV drip.

The dosage ranges for administration of the compounds of the invention are those necessary to produce the desired affect whereby symptoms of infection are ameliorated. For example, as used herein, an anti-HIV effective amount for treating or preventing an HIV infection refers to the amount administered so as to maintain an amount which suppresses or inhibits HIV infection as evidenced by standard assay. The dosage will also be determined by the existence of any adverse side effects that may accompany the compounds. It is always desirable, whenever possible, to keep adverse side effects to a minimum.

One skilled in the art can easily determine the appropriate dosage, schedule, and method of administration for the exact formulation of the composition being used in order to achieve the desired effective concentration in the individual patient. However, the dosage can vary from between about 0.001 mg/kg/day to about 1000 mg/kg/day, but preferably between about 0.001 to about 100 mg/kg/day.

In the compositions, vaccines and methods of the invention, viral immunity which is induced, altered or enhanced by hyaluronidase may be increased or modified by the use of mitogens, phytogens, colony stimulating factors, growth factors, immunomodulating or immunoenhancing cytokines, chemokines and/or soluble substances, interferons, proteglycans, perforins, granzymes, and the like, such as, but not limited to, IL-2 and PHA.

Studies

Studies were conducted at Southern Research Institute, located in Birmingham, Alabama and Frederick, Maryland, to investigate the effectiveness of the compositions and method of inhibiting HIV proliferation and their effects on cell viability.

The following is a description of certain abbreviations used in the following studies:

PBMC—peripheral blood mononuclear cell
HBSS—Hanks balanced salt solution
MOI—multiplicity of infection DPBS—Dulbecco's phosphate buffered saline
HLDA1 —hyaluronidase
ROJO—low passage HIV-1
IIIB—HIV IIIB virus
GP120 UUUB—HIV IIIB glycoprotein 120
RT—reverse transcriptase assay General Methods Hyaluronidase was obtained from bovine testes and purchased from Wyeth Laboratories Inc., a Wyeth Ayerst Company.

Rojo is an inhouse low passage virus (live HIV) obtained by Southern Research Institute.

IIIB is a laboratory isolate virus (live HIV) and was obtained from Advanced Biotechnologies, Inc.

GP120IIIB is an HIV viral glycoprotein and was obtained from Advanced Biotechnologies, Inc.

Percent virus control (% VC) in the following tables is the mean RT activity (cpm) as a percentage of a virus control. Percent cell control (% CC) is the mean XTT absorbance as a percentage of a cell control.

Monocvte Isolation Methods

Method A. Peripheral blood monocytes were isolated from normal HIV-1 negative donors by plastic adherence following ficall hypaque purification of the buffy coat PBMCs. For isolation of adherent cells, $3\times10^6$/ml non-PHA stimulated peripheral blood cells were resuspended in Hanks buffered saline (with calcium and magnesium) supplemented with 10% human AB serum, and 200 μl per well placed in a 96 well lat bottomed microtiter plate. The cells were incubated overnight at 37° C., 5% $CO_2$. Non-adherent cells were removed by washing six time with a $Ca^{++}$, $Mg^{++}$ containing medium. The adherent cells after the final wash were supplemented with RPMI 1640 supplemented with 15% fetal bovine serum (heat inactivated), 2 mM L-glutamine, 100 U/mL penicillin, 100 μg/mL streptomycin and 10 μg/mL gentamycin, and cultured for 7 days. The cultures were washed one final time before addition of compounds to remove any non-adherent cells. The cultures are carefully monitored for confluency prior to assay.

Method B. Peripheral blood monocytes were isolated from normal HIV-1 negative donors by plastic adherence following ficoll hypaque purification of the buffy coat PBMCs. Following a 2h adherence in RPMI 1640 without phenol red supplemented with 10% human pooled AB serum (heat inactivated), 2mM L-glutamine, 100 U/mL penicillin, 100 μg/mL streptomycin, 10 μg/mL gentamycin, cultures were washed to remove non-adherent cells. The monocytes were released from the plastic by vigorous pipetting with $Ca^{2+}$ and $Mg^{2+}$ free PBS. Adherent cell were assessed for viability by Trypan Blue dye exclusion, counted and resuspended in RPMI 1640 supplemented with 10% Fetal Bovine Serum (heat inactivated), 2mM L-glutamine, 100 μg/mL penicillin, 100 μm/L streptomycin, 10 μg/mL gentamycin at 1×106 monocytes per ml. The monocytes (1×105 per 0.2 cm well) are then cultured for 6 days, allowing maturation of the cells to a macrophage-like phenotype.

PBMC Isolation and Blasting

Peripheral blood monocular cells (PBMCs) are obtained from normal hepatitis and HIV-1 negative donors by ficoll hypaque gradient separation. Briefly, anti-coagulated blood is diluted 1:1 with Dulbecco's phosphate buffered saline without $Ca^{++}$ and $Mg^{++}$ (PBS) and layered over 14 mL of Lymphocyte separation media in a 50 ml centrifuge tube. Tubes are then centrifuged for 30 minutes at 600× g. Banded PBLs are gently aspirated from the resulting interface and subsequently washed 2× with PBS by low speed centrifugation. The mononuclear cells are counted, viability determined by Trypan Blue dye exclusion and resuspended in RPM1640 medium supplemented with 15% FBS (heat inactivated), 2 mM L-glutamine, 100 U/mL penicillin, 100 μg/mL streptomycin, and 10 μg/mL gentamycin with 2 μg/mL phytohemagluttin (PHA) at $1\times10^6$ cells/mL. The cells are cultured for 48 to 72 h at 37° C., 5% $CO_2$ Following incubation, cells are collected by centrifugation, washed and resuspended in RPMI 1640 supplemented with 15% FBS (heat inactivated), 2 Mm L-glutamine, 100 U/mL penicillin, 100 μg/mL streptomycin, and 10 μg/mL gentamycin with 20 U/mL recombinant IL-2 (R & D Systems, Minneapolis, Minn.). IL-2 is included in the culture medium to maintain the cell division initiated by the PHA mitogenic stimulation. The cultures are then maintained until use by ½ culture volume change with fresh IL-2 containing medium every 3 days.

PBMCs for Addition to Wells

Human peripheral blood mononuclear cells from a minimum of 2 donors, that have been blasted with PHA and IL-2, are counted, viability determined by Trypan Blue dye exclusion and mixed in equal ratios. Pooled donors are used to minimize the variability observed between individual donors which results from quantitative and qualitative differences in HIV infection and overall response to the PHA and IL-2 of primary lymphocyte populations. The cells are resuspended at $1\times10^6$ cells/mL in RPMI 1640 without phenol red supplemented with 15% Fetal Bovine Serum (heat inactivated), 2 mM L-glutamine, 100 U/mL penicillin, 100 μg/mL streptomycin, 10 μg/mL gentamycin and IL-2 (20 U/mL, R&D Systems, Minneapolis, Minn.). Fifty microliters of cells are then distributed to the inner 60 wells of a 96 well round bottom Microtiter culture plate in a standard format developed by the Infectious Disease Research department of Southern Research Institute. Each plate contains cell control wells (cells only), virus control wells (cell plus virus), and experimental wells (drug plus cells plus virus).

Reverse Transcriptase Assay

Reverse transcriptase (RT) activity was measured in cell-free supernatants. Tritiated thymidine triphosphate (NEN) (TTP) was resuspended in distilled $H_2O$ at 5 Cl/mL. Poly rA and oligo dT were prepared as a stock solution which was kept at −20° C. The RT reaction buffer was prepared fresh on a daily basis and consists of 125 μL 1.0 M EGTA, 125 μL d $H_2O$, 110 μL 10% SDS, 50 μL 1.0 M Tris (pH 7.4), 50 μL 1.0 M DTT, and 40μl1.0 M $MgCl_2$. These three solutions were mixed together in a ratio of 2 parts TTP, 1 part poly rA:oligo dT, and 1 part reaction buffer. Ten microliters of this reaction mixture was placed in a round bottom microtiter plate and 15 μL of virus containing supernatant was added and mixed. The plate was incubated at 37° C. in a water bath with a solid support to prevent submersion of the plate and incubated for 60 minutes. Following reaction, the reaction volume was spotted onto pieces of DE81 paper, washed 5 times for 5 minutes each in a 5% sodium phosphate buffer, 2 times for 1 minute each in distilled water, 2 times for 1 minute each in 70% ethanol, and then dried. Opti-Fluor O was added to each sample and incorporated radioactivity was quantitated utilizing a Wallace 1450 Microbetaplus liquid scintillation counter.

Data Analysis

Using an in-house computer program, $IC_{50}$ (50% inhibition of virus replication), $TC_{50}$ (50% reduction in cell viability) and a therapeutic index (TI, $IC_{50}/TC_{50}$) were determined. Data for both antiviral activity and toxicity are provided in the following tables. AZT was used as a relevant positive control compound for the individual assays.

STUDY 1: PBMC Assay

This study compares the ability of hyaluronidase to AZT to lower viral replication as measured by reverse transcriptase levels. RT was measured on days 7, 14, and 21. Three different treatment regimens were used in the comparative study (Treatments A, B and C). The data indicate that hyaluronidase results in a greater reduction in viral replication as measured by reverse transcriptase, i.e., that it inhibits viral proliferation to a greater degree than AZT, through its adverse effects on HIV infected cells.

Treatment A. Normal mixed PHA blasted human PBMCs (5×10e4/well) were pretreated with drug every 48 hours for 3 doses. On day 6 of pretreatment, cells were infected with clinical isolate ROJO. 48 hours post infection, treatment with drugs continued for an additional 3 treatments. Samples for assay were collected on D7 (day 7), 14, 21, post infection, frozen and later analyzed for reverse transcriptase. RT activity data, as a percentage of virus control (% VC), are shown in Table 1.

TABLE 1

Effectiveness of Hyaluronidase compared with AZT against HIV-Treatment A.

| | Hyaluronidase | | | | AZT | | |
|---|---|---|---|---|---|---|---|
| units/ mL | Day 7 % VC | Day 14 % VC | Day 21 % VC | μM | Day 7 % VC | Day 14 % VC | Day 21 % VC |
| 15 | 1.1 | 0.7 | 1.1 | 0.5 | 2.3 | 21.4 | 78.3 |
| 4.8 | 1.1 | 0.3 | 1.0 | 0.16 | 2.7 | 40.3 | 126.3 |
| 1.536 | 1.6 | 0.2 | 1.2 | 0.0512 | 3.0 | 40.7 | 134.8 |
| 0.49152 | 1.0 | 0.3 | 0.4 | 0.01638 | 11.6 | 57.9 | 129.5 |
| 0.15729 | 0.7 | 0.2 | 0.7 | 0.00524 | 10.2 | 78.3 | 155.1 |
| 0.05033 | 1.0 | 0.4 | 0.9 | 0.00168 | 25.1 | 74.2 | 135.6 |
| 0.01611 | 1.1 | 0.1 | 0.6 | 0.00054 | 19.3 | 99.8 | 141.5 |
| 0.00515 | 49.5 | 14.9 | 5.1 | 0.00017 | 47.3 | 115.4 | 164.5 |
| 0.00165 | 131.1 | 21.6 | 24.4 | 5.5E-05 | 77.0 | 100.4 | 159.7 |

Treatment B. Normal mixed PHA blasted human PBMCs (as above) were plated in 96 wells and allowed to incubate for 48 hours (cells were set at same time as treatment A from same pool). Drug pretreatment started on day 2 and was repeated on day 4. On day 6, cell were infected as in treatment A, with concurrent addition of drug for a total of 3 treatments. Samples for assay were collected on D7, 14, 21 postinfection, frozen and later analyzed for reverse transcriptase. RT activity data, as a percentage of virus control (% VC), are shown in Table 2.

TABLE 2

Effectiveness of Hyaluronidase compared with AZT against HIV-Treatment B.

| | Hyaluronidase | | | | AZT | | |
|---|---|---|---|---|---|---|---|
| units/ mL | Day 7 % VC | Day 14 % VC | Day 21 % VC | μM | Day 7 % VC | Day 14 % VC | Day 21 % VC |
| 15 | 3.4 | 0.5 | 0.7 | 0.5 | 5.4 | 9.5 | 87.5 |
| 4.8 | 1.9 | 0.5 | 1.2 | 0.16 | 3.9 | 25.7 | 93.8 |
| 1.536 | 4.1 | 0.2 | 0.4 | 0.0512 | 5.4 | 28.5 | 158.0 |
| 0.49152 | 4.9 | 0.4 | 0.3 | 0.01638 | 9.6 | 58.0 | 133.9 |
| 0.15729 | 2.8 | 0.4 | 0.5 | 0.00524 | 9.3 | 51.0 | 109.0 |
| 0.05033 | 3.0 | 0.4 | 0.9 | 0.00168 | 10.7 | 57.5 | 153.5 |
| 0.01611 | 3.6 | 0.6 | 0.2 | 0.00054 | 34.2 | 70.1 | 111.8 |
| 0.00515 | 6.0 | 1.0 | 0.8 | 0.00017 | 43.6 | 80.8 | 129.8 |
| 0.00165 | 47.1 | 10.5 | 5.1 | 5.5E-05 | 90.9 | 97.0 | 163.3 |

Treatment C. Pretreatment schedule was identical to treatment A, for a total of 3 treatments. On Day 6, cells were infected as above, with no further addition of drugs. Samples for assay were collected on D7. 14, 21 post infection, frozen and later analyzed for reverse transcriptase. RT activity data, as a percentage of virus control (% VC), are shown in Table 3.

TABLE 3

Effectiveness of Hyaluronidase compared with AZT against HIV-Treatment C.

| | Hyaluronidase | | | | AZT | | |
|---|---|---|---|---|---|---|---|
| units/ mL | Day 7 % VC | Day 14 % VC | Day 21 % VC | μM | Day 7 % VC | Day 14 % VC | Day 21 % VC |
| 15 | 3.2 | 0.6 | 0.7 | 0.5 | 8.9 | 26.8 | 90.1 |
| 4.8 | 4.6 | 0.4 | 0.7 | 0.16 | 10.3 | 38.1 | 72.0 |
| 1.536 | 2.7 | 0.4 | 0.6 | 0.0512 | 17.0 | 70.5 | 89.2 |
| 0.49152 | 4.1 | 0.2 | 0.4 | 0.01638 | 22.1 | 62.9 | 119.2 |
| 0.15729 | 3.0 | 0.2 | 0.8 | 0.00524 | 28.4 | 74.6 | 104.7 |
| 0.05033 | 3.4 | 0.4 | 0.6 | 0.00168 | 45.4 | 125.4 | 119.1 |
| 0.01611 | 3.9 | 1.8 | 1.0 | 0.00054 | 73.6 | 92.3 | 106.2 |
| 0.00515 | 100.4 | 26.0 | 13.2 | 0.00017 | 67.5 | 92.9 | 110.1 |
| 0.00165 | 104.0 | 42.4 | 23.5 | 5.5E-05 | 88.6 | 109.2 | 198.4 |

STUDY 2. Hyaluronidase Chronic Overlay Testing.

These studies were designed to test the ability of phagocytes and antigen-presenting cells, such as macrophages and monocytes to recognize hyaluronidase treated infected cells.

This chronic overlay study demonstrates that when HIV infected PBMCs are treated with various dilutions of hyaluronidase then washed and purged of enzyme and unbound virus and incubated with monocytes/macrophage populations the monocytes/macrophages process the infected cells and/or virus in such a way that the monocytes/macrophages are capable of passing this processed information to other immunocytes. This is evidenced by the fact that when these same monocytes/macrophages are incubated with naïve PBMCs, the naïve PBMCs become resistant to HIV challenge. This immunity only develops when the original infected PBMC's are treated with hyaluronidase.

Assay method. Seven day old Rojo chronically infected (and uninfected control) PBMCs are pre-treated with two fold dilutions of HLDA-1 for 48 hours. Treated cells are 2× washed with PBS and overlayed onto seven day old macrophages for 72 hours at which time the PBMCs were washed off and replaced with fresh uninfected pha blast PBMCs in the presence of IL-1 (5.0 ng/mL) and IL-2 (20U/mL). Overlayed cells are incubated for 48 hours 50% of cells transferred to a fresh 96 well plate, and then both the original and transfer plate infected with ROJO at a standard MOI. Samples for reverse transcriptase and toxicity testing were processed on day 7 post secondary infection. RT activity data, as a percentage of virus control (% VC), and cell viability (% CC) are shown in Tables 4 and 5.

These studies also show that immunity is imparted to naïve PBMCs (PBMCs that were never exposed to virus, hyaluronidase or other infected cells). The naïve PBMC's resistance to HIV infection is due to information transferred to them via communication molecules and cell to cell contact from co-incubation with the exposed macrophage/monocytes culture.

Assay Summary. Virus (clinical isolate Rojo or purified GP120 IIIB) was incubated for 48 hours with two-fold

TABLE 4

Hyaluronidase treated Rojo chronic PBMCs compared with hyaluronidase treated uninfected PBMCs (control). Both systems washed off prior to virus challenge.

| | Hyaluronidase + Rojo chronic PBMCs | | | | Hyaluronidase + control uninfected PBMCs | | | |
|---|---|---|---|---|---|---|---|---|
| | Macrophage + PBMCs | | Transfer PBMCs | | Macrophage + PBMCs | | Transfer PBMCs | |
| units/mL | % VC | % CC | % VC | % CC | % VC | % CC | % VC | % CC |
| 30 | 19.9 | 112.5 | 18.0 | 100.6 | 43.8 | 116.4 | 24.0 | 114.7 |
| 20 | 14.2 | 103.3 | 13.6 | 97.3 | 41.9 | 117.3 | 33.0 | 111.1 |
| 15 | 13.3 | 107.4 | 21.9 | 104.9 | 40.2 | 126.3 | 20.6 | 114.6 |
| 10 | 14.8 | 108.4 | 21.5 | 111.7 | 56.2 | 130.4 | 21.2 | 112.3 |
| 7.5 | 12.7 | 103.6 | 21.9 | 111.9 | 56.4 | 117.1 | 26.8 | 111.6 |
| 5 | 22.2 | 115.5 | 24.2 | 115.7 | 71.1 | 108.9 | 18.0 | 121.5 |
| 3.75 | 124.1 | 89.5 | 126.5 | 108.0 | 111.5 | 107.2 | 34.4 | 118.7 |
| 2.5 | 207.4 | 73.6 | 183.0 | 107.1 | 102.3 | 122.3 | 47.3 | 107.3 |
| Control | 223.4[a] | 83.6[b] | 180.6[a] | 116.2[b] | 60.8[a] | 99.9[b] | 29.2[a] | 98.5[b] |

[a]Virus Control;
[b]Cell control.

TABLE 5

Hyaluronidase treated Rojo chronic PBMCs compared with hyaluronidase treated uninfected PBMCs (control). Both systems washed off prior to virus challenge.

| | Hyaluronidase + Rojo chronic PBMCs | | | | Hyaluronidase + control uninfected PBMCs | | | |
|---|---|---|---|---|---|---|---|---|
| | Macrophage + PBMCs | | Transfer PBMCs | | Macrophage + PBMCs | | Transfer PBMCs | |
| units/mL | % VC | % CC | % VC | % CC | % VC | % CC | % VC | % CC |
| 30 | 291.8 | 188.6 | 222.3 | 108.7 | 163.1 | 329.7 | 142.7 | 114.5 |
| 20 | 375.9 | 188.2 | 284.2 | 112.3 | 196.8 | 340.2 | 383.0 | 117.6 |
| 15 | 1345.0 | 185.9 | 1714.3 | 131.1 | 1085.6 | 339.6 | 2376.3 | 134.2 |
| 10 | 1384.5 | 247.5 | 730.4 | 177.2 | 965.0 | 306.1 | 2889.3 | 165.2 |
| 7.5 | 476.0 | 148.2 | 792.6 | 187.2 | 1095.5 | 215.6 | 3513.0 | 146.3 |
| 5 | 253.5 | 135.8 | 181.3 | 110.2 | 184.7 | 139.0 | 380.0 | 109.3 |
| 3.75 | 191.7 | 120.6 | 152.4 | 111.4 | 108.5 | 108.2 | 195.0 | 107.3 |
| 2.5 | 164.0 | 121.0 | 106.0 | 104.7 | 91.6 | 85.6 | 136.0 | 101.7 |
| Control | 100.1[a] | 86.3[b] | 102.4[a] | 99.6[b] | 102.5[a] | 97.5[b] | 101.3[a] | 98.0[b] |

[a]Virus Cell;
[b]Cell control.

STUDY 3. Hyaluronidase Sensitization Assays

The following hyaluronidase sensitization assays reveal that a cell free immunogen is created when HIV is treated with hyaluronidase. In this assay, HIV is treated directly with hyaluronidase for various periods of time before exposure to macrophage/monocytes populations. The results indicate that hyaluronidase treated virus alone initiates an immune response when followed with macrophage/monocyte incubation and processing. However, these studies also indicate the subject monocytes/macrophages are capable of infecting naïve PBMCs at the same time, when the live virus is used. This becomes particularly true when the monocytes/macrophages are stimulated with PHA and IL-2.

dilutions of Hyaluronidase (0.5 ML of diluted drug pluse 50, 10, and 5 μL Rojo stock or 5 μL of GP120 IIIB). The Hyaluronidase/virus mixture was then transferred to macrophage monolayers and incubated an additional 3 days. The the monolayers were 3× washed with PBS, with Human PBMCs (5x10e4/well) returned to the monolayer. The PBMCs were either mixed donor, PHA blast, with IL2 supplemented medium, or were single donor non-PHA blast/no IL2 supplemented. After 72 hours, the PBMCs were removed, reset in a 96 well plate and then challenged with a standard MOI of the Rojo virus. The plates were incubated for an additional 6 days and then assayed for RT activity. The studies were produced in triplicate. RT activity data, as a percentage of virus control (% VC), are shown in Tables 6 and 7.

TABLE 6

Rojo Treated with Hyaluronidase; naïve PBMCs with and without PHA/IL2.

| | Without PHA/IL2 | | | With PHA/IL2 | | |
|---|---|---|---|---|---|---|
| Treatment (μg/mL) | 5 μL Rojo % VC | 10 μL Rojo % VC | 50 μL Rojo % VC | 5 μL Rojo % VC | 10 μL Rojo % VC | 50 μL Rojo % VC |
| 25 | 8.8 | 2.3 | 8.4 | 71.2 | 97.3 | 73.4 |
| 12.5 | 12.3 | 15.2 | 37.0 | 72.2 | 115.9 | 78.2 |
| 6.3 | 15.7 | 67.1 | 21.3 | 81.6 | 117.6 | 61.3 |
| 3.1 | 9.7 | 97.3 | 86.8 | 56.0 | 117.8 | 97.3 |
| 1.56 | 6.4 | 115.6 | 146.0 | 59.0 | 125.9 | 115.7 |
| 0.78 | 7.0 | 97.6 | 111.9 | 68.2 | 110.5 | 102.6 |
| 0.39 | 102.7 | 115.9 | 149.4 | 79.7 | 123.2 | 87.6 |
| 0.20 | 77.8 | 112.8 | 125.8 | 88.8 | 106.0 | 79.1 |
| VC | 100.0 | 100.0 | 100.0 | 100.0 | 100.0 | 100.0 |

TABLE 7

5 μL $GP_{120}$ IIIB Treated with Hyaluronidase; PBMCs with and without PHA/IL2.

| Treatment (μg/mL) | Without PHA/IL2 % VC | With PHA/IL2 % VC |
|---|---|---|
| 25 | 8.8 | 85.5 |
| 12.5 | 88.8 | 93.1 |
| 6.3 | 71.7 | 105.3 |
| 3.1 | 145.7 | 85.5 |
| 1.56 | 158.5 | 98.0 |
| 0.78 | 134.4 | 101.9 |
| 0.39 | 195.6 | 116.1 |
| 0.20 | 155.9 | 78.6 |
| VC | 100.0 | 100.0 |

STUDY 4.

In the following set of experiments, virus {IIIB(Dec. 1, 2000-4 uL/well), GP120 IIIB (0.5 u g/mL) and Rojo(Oct. 23, 2000-1.25 uL/well)} was treated overnight in 2 fold dilutions of the compound Hyaluronidase and then transferred to two types of macrophage (Turpin and Standard methodology) 96 well plates for 24 hours. (Turpin methodology differs from standard methodology in that it utilizes purer, more sensitive macrophages having a higher percentage of monocytes and macrophages). The macrophage plates were then washed with HBSS multiple times. Fresh mixed pha blast PBMCs (5×10e4/well) were placed on the macrophage cells, allowed to incubate for 72 hours and then harvested and reset in a fresh 96 well plate. The PBMCs were then challenged overnight with the respective virus (IIIB or Rojo) at a standard MOI for that virus. The PBMCs were 5× in plate spin washed with DPBS, incubated 24 hours, at which time 5×10e4 fresh pha blast PBMCs/well were added. The culture was incubated an additional 6 days and then assayed for RT activity.

Where viability corrections were conducted, they were performed by dividing the RT CPM value by the toxicity absorbance in order to compensate for well to well variations noted in the cell titer toxicity noted. Variance is believed to be due to well to well harvest inconsistencies when removing the PBMCs from the macrophage plates. RT activity data, as a percentage of virus control (% VC), and cell viability (% CC) are shown in Tables 8 and 9.

TABLE 8

Treatment with Hyaluronidase of IIIB, GP120IIIB and Rojo; Turpin and standard macrophage methodology.

| | IIIB Sensitized Hyaluronidase Macrophage | | | | $GP120_{IIIB}$Sensitized Hyaluronidase Macrophage | | | | Rojo Sensitized Hyaluronidase Macrophage | | | |
|---|---|---|---|---|---|---|---|---|---|---|---|---|
| | Turpin | | Standard | | Turpin | | Standard | | Turpin | | Standard | |
| μg/mL | % VC | % CC | % VC | % CC | % VC | % CC | % VC | % CC | % VC | % CC | % VC | % CC |
| 25 | 23.6 | 91.6 | 99.8 | 82.1 | 52.1 | 91.4 | 70.6 | 87.1 | 15.5 | 75.0 | 21.0 | 92.9 |
| 12.5 | 73.8 | 128.5 | 153.1 | 101.5 | 62.8 | 73.1 | 100.4 | 123.1 | 47.4 | 81.8 | 49.4 | 103.1 |
| 6.25 | 70.0 | 110.2 | 234.4 | 133.5 | 72.2 | 73.2 | 106.5 | 115.1 | 39.4 | 81.0 | 57.7 | 102.8 |
| 3.125 | 86.5 | 80.3 | 120.8 | 104.9 | 71.2 | 87.4 | 82.3 | 109.2 | 45.6 | 82.3 | 55.8 | 103.8 |
| 1.5625 | 68.3 | 90.2 | 203.0 | 106.6 | 58.0 | 73.4 | 100.7 | 104.2 | 61.1 | 88.7 | 62.8 | 110.1 |
| 0.78125 | 100.0 | 109.1 | 129.9 | 110.7 | 105.6 | 90.8 | 94.5 | 95.0 | 48.6 | 86.3 | 59.9 | 107.4 |
| 0.390625 | 84.5 | 84.8 | 181.3 | 111.9 | 83.5 | 67.6 | 87.7 | 120.0 | 69.6 | 81.3 | 50.4 | 98.6 |
| 0.195313 | 95.8 | 86.5 | 178.1 | 124.7 | 108.1 | 98.4 | 102.8 | 122.8 | 82.9 | 98.6 | 91.8 | 111.1 |
| 0.097656 | 98.7 | 102.4 | 145.2 | 138.2 | 89.0 | 85.6 | 176.4 | 167.6 | 86.5 | 92.3 | 82.2 | 124.4 |
| VC | 100.0 | 100.0 | 100.0 | 100.0 | 100.0 | 100.0 | 100.0 | 100.0 | 100.0 | 100.0 | 100.0 | 100.0 |

The data in Table 9 indicates that the assays are still valid when corrected for viability. The assays still demonstrate low to moderate virus control of each virus and the GP 120 antigen.

TABLE 9

Treatment with Hyaluronidase of IIIB, GP120IIIB and Rojo; Turpin and standard macrophage methodology; viability corrected

| | IIIB Sensitized Hyaluronidase (viability corrected) Macrophage | | | | $GP120_{IIIB}$Sensitized Hyaluronidase (viability corrected) Macrophage | | | | Rojo Sensitized Hyaluronidase (viability corrected) Macrophage | | | |
|---|---|---|---|---|---|---|---|---|---|---|---|---|
| | Turpin | | Standard | | Turpin | | Standard | | Turpin | | Standard | |
| μg/mL | % VC | % CC | % VC | % CC | % VC | % CC | % VC | % CC | % VC | % CC | % VC | % CC |
| 25 | 26.6 | 91.6 | 124.6 | 82.1 | 54.1 | 91.4 | 81.6 | 87.1 | 25.6 | 75.0 | 24.0 | 92.9 |
| 12.5 | 67.2 | 128.5 | 156.9 | 101.5 | 84.9 | 73.1 | 82.7 | 123.1 | 58.0 | 81.8 | 49.8 | 103.1 |
| 6.25 | 63.4 | 110.2 | 181.7 | 133.5 | 96.0 | 73.2 | 95.2 | 115.1 | 48.5 | 81.0 | 56.6 | 102.8 |
| 3.125 | 106.2 | 80.3 | 115.2 | 104.9 | 79.0 | 87.4 | 76.1 | 109.2 | 55.5 | 82.3 | 53.4 | 103.8 |
| 1.5625 | 79.6 | 90.2 | 189.1 | 106.6 | 74.4 | 73.4 | 97.2 | 104.2 | 69.1 | 88.7 | 57.0 | 110.1 |
| 0.78125 | 95.5 | 109.1 | 117.6 | 110.7 | 115.4 | 90.8 | 100.5 | 95.0 | 56.9 | 86.3 | 55.1 | 107.4 |
| 0.390625 | 98.3 | 84.8 | 177.8 | 111.9 | 122.4 | 67.6 | 74.2 | 120.0 | 85.0 | 81.3 | 52.2 | 98.6 |
| 0.195313 | 110.9 | 86.5 | 141.1 | 124.7 | 111.2 | 98.4 | 83.8 | 122.8 | 84.5 | 98.6 | 82.5 | 111.1 |
| 0.097656 | 95.3 | 102.4 | 103.7 | 138.2 | 116.0 | 85.6 | 105.6 | 167.6 | 94.1 | 92.3 | 66.0 | 124.4 |
| VC | 100.0 | 100.0 | 100.0 | 100.0 | 100.0 | 100.0 | 100.0 | 100.0 | 100.0 | 100.0 | 100.0 | 100.0 |

STUDY5

To further define and clarify the mechanism of action of the above data and determine whether or not a cell-free immunogen could be created, various combinations of live, heat treated and aldrathiol-2 treated virus were reacted with hyaluronidase for 24–48 hours. Control groups were not treated with the enzyme. The virus was then titrated on macrophage/monocyte cultures and incubated at 37° C. for 48 hours at which time the macrophages and monocytes were washed 3×, resuspended and placed in fresh wells. Naïve PBMC's were overlayed on the macrophage/monocyte cultures and incubated at 37° C. for 72 hours. The PBMC's were then separated, washed and placed in fresh wells with fresh medium and rested for 48 hours. After a 48 hour rest period, the PBMC's were challenged with HIV-1 with and without PHA, I1-2, or both. After 144 hours HIV infection was confirmed by reverse transcriptase activity and P-24 assay. These various assays are presented below in Table 10.

Macrophages and monocytes incubated with heat inactivated or Aldrathiol-2 treated virus only did not impart or transfer protection or immunity to naïve PBMC's against HIV infection. Monocytes and macrophages that were incubated with hyaluronidase treated heat inactivated or Aldrathiol-2 treated virus provided the naïve PBMC's up to 100% resistance to HIV-1 challenge. This immunity is not seen with whole inactivated virus alone or with viral antigens such as GP120. Heat inactivation of HIV produces far superior results over APL-2 inactivation when in combination with hyaluronidase. The studies reveal that hyaluronidase does not simply deplete receptors necessary for infectivity. The macrophage/monocyte cultures used in these experiments are 6 or 7 days old, both macrophage/monocyte and PBMC cultures were repeatedly washed, culture medium was changed 2 and 3 times, HIV infected dead cells or HIV alone served as antigen or immunogen and naïve PBMC's were resistant to HIV challenge 17 days post infection; all of which reasonably rule out a general cytokine, chemokine, or interferon protective effect.

TABLE 10

| Hyaluranidase | Assay #1[1] | | Assay #2[2] | | Assay #3[3] | | Assay #4[4] | |
|---|---|---|---|---|---|---|---|---|
| Concentration (mg/mL) | Mean RT | % Control | Mean RT | % Control | Mean RT | % Control | Mean RT | % Control |
| 20 | 3635.7 | 16.9 | 3298.3 | 10.4 | 11940.7 | 90.3 | 3961.7 | 29.9 |
| 10 | 6000 | 27.9 | 8391.3 | 26.4 | 12058 | 91.2 | 2973.7 | 22.4 |
| 5 | 20882.7 | 97.3 | 6548.3 | 20.6 | 5641.7 | 42.7 | 247.3 | 1.9 |
| 0(Control) | 21473 | 100 | 31797.7 | 100 | 13217.3 | 100 | 13259.3 | 100 |
| Sum | 30518.4 | 142.1 | 18237.9 | 57.4 | 29640.4 | 224.2 | 7182.7 | 54.2 |
| Hyaluranidase | Assay #5[5] | | Assay #6[6] | | Assay #7[7] | | Assay #8[8] | |
| Concentration (mg/mL) | Mean RT | % Control | Mean RT | % Control | Mean RT | % Control | Mean RT | % Control |
| 20 | 35.4.0 | 18.5 | 4430.7 | 19.5 | 27462 | 162.7 | 9014.3 | 51.2 |
| 10 | 11156.3 | 58.3 | 11244.7 | 49.6 | 20614.7 | 122.2 | 11241 | 63.8 |

TABLE 10-continued

| | | | | | | | | |
|---|---|---|---|---|---|---|---|---|
| 5 | 12442.7 | 65.1 | 12279.7 | 54.1 | 18777.7 | 111.3 | 30167.3 | 171.3 |
| 0(Control) | 19125 | 100 | 22688.3 | 100 | 16875.3 | 100 | 17607.7 | 100 |
| Sum | 23599 | 141.9 | 27955.1 | 123.2 | 66854.4 | 396.2 | 50422.6 | 286.3 |

| Hyaluranidase | Assay #9[9] | | Assay #10[10] | | Assay #11[11] | | Assay #12[12] | |
|---|---|---|---|---|---|---|---|---|
| Concentration (mg/mL) | Mean RT | % Control | Mean RT | % Control | Mean RT | % Control | Mean RT | % Control |
| 20 | 7725.7 | 96.2 | 3633.7 | 61.1 | 8496.3 | 30.1 | 8382 | 56.1 |
| 10 | 10344 | 128.8 | 7258.7 | 122.2 | 21230 | 75.3 | 5946.7 | 39.8 |
| 5 | 11038 | 137.4 | 13715.3 | 230.8 | 17826.3 | 63.2 | 17657 | 118.3 |
| 0(Control) | 8034 | 100 | 5941.3 | 100 | 28199.3 | 100 | 14928 | 100 |
| Sum | 29107.7 | 362.4 | 24607.7 | 414.1 | 47552.6 | 168.6 | 31985.7 | 214.2 |

[1]Macrophages pretreated with hyaluronidase; virus treated with hyaluronidase after heat treatment at 60° C.; no washing of PBMCs prior to challenge.
[2]Same as 1 except the PBMCs were washed prior to challenge.
[3]Macrophages pretreated with hyaluronidase; virus treated with hyaluronidase before heat treatment; no washing of PBMCs prior to challenge.
[4]Same as 3 except the PBMCs were washed.
[5]Macrophages pretreated with hyaluronidase; virus treated with aldrithiol-2 before heat treatment at 60° C.; no washing of PBMCs prior to challenge.
[6]Same as 5 except the PBMCs were washed.
[7]No macrophage pre-treatment with hyaluronidase; virus treated with hyaluronidase after heat treatment at 60° C.; no washing of PBMCs prior to challenge.
[8]Same as 7 except the PBMCs were washed prior to challenge.
[9]No macrophage pre-treatment with hyaluronidase; virus treated with hyaluronidase before heat treatment at 60° C.; no washing of PBMCs prior to challenge.
[10]Same as 9 except the PBMCs were washed prior to challenge.
[11]No macrophage pre-treatment with hyaluronidase; virus treated with aldrithiol-2 before heat treatment at 60° C.; no washing of PBMCs prior to challenge.
[12]Same as 11 except the PBMCs were washed prior to challenge.

In conclusion, the above studies reveal the varied utility of the hyaluronidase enzyme in the treatment and prevention of retroviral infections such as HIV. The various uses of hyaluronidase revealed herein include that: it can be used as an immunomodulator; it can be used to kill infected cells and initiate an immune response to the infectious agent; hyaluronidase treated live or dead virus can be used to illicit an immune response to the virus; hyaluronidase can be used to up-regulate the immune system; immunogens or antigens can be created by treating proteins, carbohydrates, and/or glycoproteins with hyaluronidase; viral immunogens or antigens can be created by treating a virus with hyaluronidase; treatment of viral proteins, viral glycoproteins or viral carbohydrates with hyaluronidase can be used to enhance or induce internalization and/or phagocytosis and immune processing by antigen-presenting cells; hyaluronidase treated live, weakened, attenuated or dead virus can be used to create a less virulent and/or a non-infectious antigen or immunogen. The compositions of the invention can be further used: to induce antigen presentation by APCs to PBMCs which is necessary for the proper immune response; to engender an immune response in a patient by priming or activating APCs; to create a cell or cell-free antigen or immunogen; to induce or enhance internalization or phagocytosis of infected cells by phagocytic cells; to induce or enhance internalization and phagocytosis of dead cells by APCs. Hyaluronidase compositions of the invention can also be used to induce or enhance immunity in a patient by initiating responses to otherwise self or host lineage altered cells, antigens or immunogens. Hyaluronidase compositions of the invention can also be used to initiate immune responses to pathogens or pathogen infected cells in a patient.

It is contemplated that various modifications may be made to the compositions, vaccines and methods of the present invention without departing from the spirit and scope of the invention as defined in the following claims.

What is claimed is:

1. A composition comprising:

a) HIV infected cells that have been treated with a bovine hyaluronidase or a hyaluronidase enzyme with comparable activity at a concentration of at least 0.01611 units/mL, and b) optionally a pharmaceutically acceptable carrier or diluent.

2. The composition of claim 1 wherein the HIV infected cells are human host cells.

3. The composition of claim 2 wherein the HIV infected cells are human peripheral blood mononuclear cells or antigen presenting cells.

4. The composition of claim 2 wherein the HIV infected cells exhibit reduced cell viability.

5. The composition of claim 4 wherein the HIV infected cells form HIV immunogens.

6. The composition of claim 5 wherein the immunogens prime and activate antigen presenting cells.

7. The composition of claim 6 wherein the antigen presenting cells are macrophages, monocytes or both.

8. The composition of claim 7 wherein the antigen presenting cells are capable of engendering an immune response that imparts to naïve cells resistance to HIV challenge.

9. The composition of claim 7 wherein the antigen presenting cells are capable of transferring HIV immunity to naïve cells following co-incubation with the treated cells.

* * * * *